(12) United States Patent
Medhkour et al.

(10) Patent No.: US 6,493,589 B1
(45) Date of Patent: *Dec. 10, 2002

(54) METHODS AND APPARATUS FOR TREATMENT OF PULMONARY CONDITIONS

(75) Inventors: Adel M. Medhkour, Brooklyn Park, MN (US); Michael F. Hoey, Shoreview, MN (US); Peter M. J. Mulier, Stillwater, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/636,573

(22) Filed: Aug. 10, 2000

Related U.S. Application Data

(63) Continuation-in-part of application No. 09/304,681, filed on May 4, 1999, now Pat. No. 6,327,505.
(60) Provisional application No. 60/084,580, filed on May 7, 1998.

(51) Int. Cl.⁷ .............................. A61N 1/06; A61N 1/18
(52) U.S. Cl. ....................... 607/99; 607/105; 607/113; 606/41; 604/114
(58) Field of Search .................. 606/32, 34, 41, 606/42, 49; 607/99, 105, 113; 604/114

(56) References Cited

U.S. PATENT DOCUMENTS

| | | | |
|---|---|---|---|
| 5,098,431 A | 3/1992 | Rydell | 606/48 |
| 5,403,311 A | 4/1995 | Abele et al. | 606/49 |
| 5,431,649 A | 7/1995 | Mulier et al. | 606/41 |
| 5,433,708 A | 7/1995 | Nichols et al. | 604/113 |
| 5,542,928 A | 8/1996 | Evans et al. | 604/113 |
| 5,584,872 A | 12/1996 | LaFontaine et al. | 607/116 |
| 5,609,151 A | 3/1997 | Mulier | 128/642 |
| 5,653,692 A | 8/1997 | Masterson et al. | 604/113 |
| 5,676,693 A | 10/1997 | LaFontaine | 607/116 |
| 5,697,281 A | 12/1997 | Eggers et al. | 604/114 |
| 5,697,536 A | 12/1997 | Eggers et al. | 604/114 |
| 5,697,909 A | 12/1997 | Eggers et al. | 604/114 |
| 5,697,927 A | 12/1997 | Imran et al. | 606/41 |
| 5,725,524 A | 3/1998 | Mulier et al. | 606/41 |
| 5,800,482 A | 9/1998 | Pomeranz et al. | 607/101 |
| 5,807,395 A | 9/1998 | Mulier et al. | 606/41 |
| 5,876,398 A | 3/1999 | Mulier et al. | 606/41 |
| 5,888,198 A | 3/1999 | Eggers et al. | 604/114 |
| 5,891,095 A | 4/1999 | Eggers et al. | 604/114 |
| 5,895,417 A | 4/1999 | Pomeranz et al. | 607/101 |
| 5,897,553 A | 4/1999 | Mulier et al. | 606/41 |
| 5,902,328 A | 5/1999 | LaFontaine et al. | 607/116 |
| 5,906,613 A | 5/1999 | Mulier et al. | 606/41 |
| 5,913,854 A | 6/1999 | Maquire et al. | 606/41 |
| 5,957,919 A | * 9/1999 | Laufer | 606/27 |
| 6,283,988 B1 | * 9/2001 | Laufer et al. | 607/105 |
| 6,283,989 B1 | * 9/2001 | Laufer et al. | 607/105 |
| 6,299,633 B1 | * 10/2001 | Laufer | 607/99 |
| 6,327,505 B1 | * 12/2001 | Medhkour et al. | 606/41 |

* cited by examiner

Primary Examiner—Lee Cohen
(74) Attorney, Agent, or Firm—Girma Wolde-Michael; Michael C. Soldner

(57) ABSTRACT

Apparatuses and methods are disclosed for introducing a conductive fluid and delivering an electrical current to the fluid at a target site in a body lumen. The electrical current is delivered to the site by a conductive electrode through the conductive fluid, causing the tissues in the lumen walls, or peripheral to the lumen walls, to heat and contract. Application of the current can be discontinued when the lumen wall has contracted or been reduced to the desired extent, which will often be complete occlusion. Alternatively, the current can be applied until tissues peripheral to the lumen are effected.

22 Claims, 15 Drawing Sheets

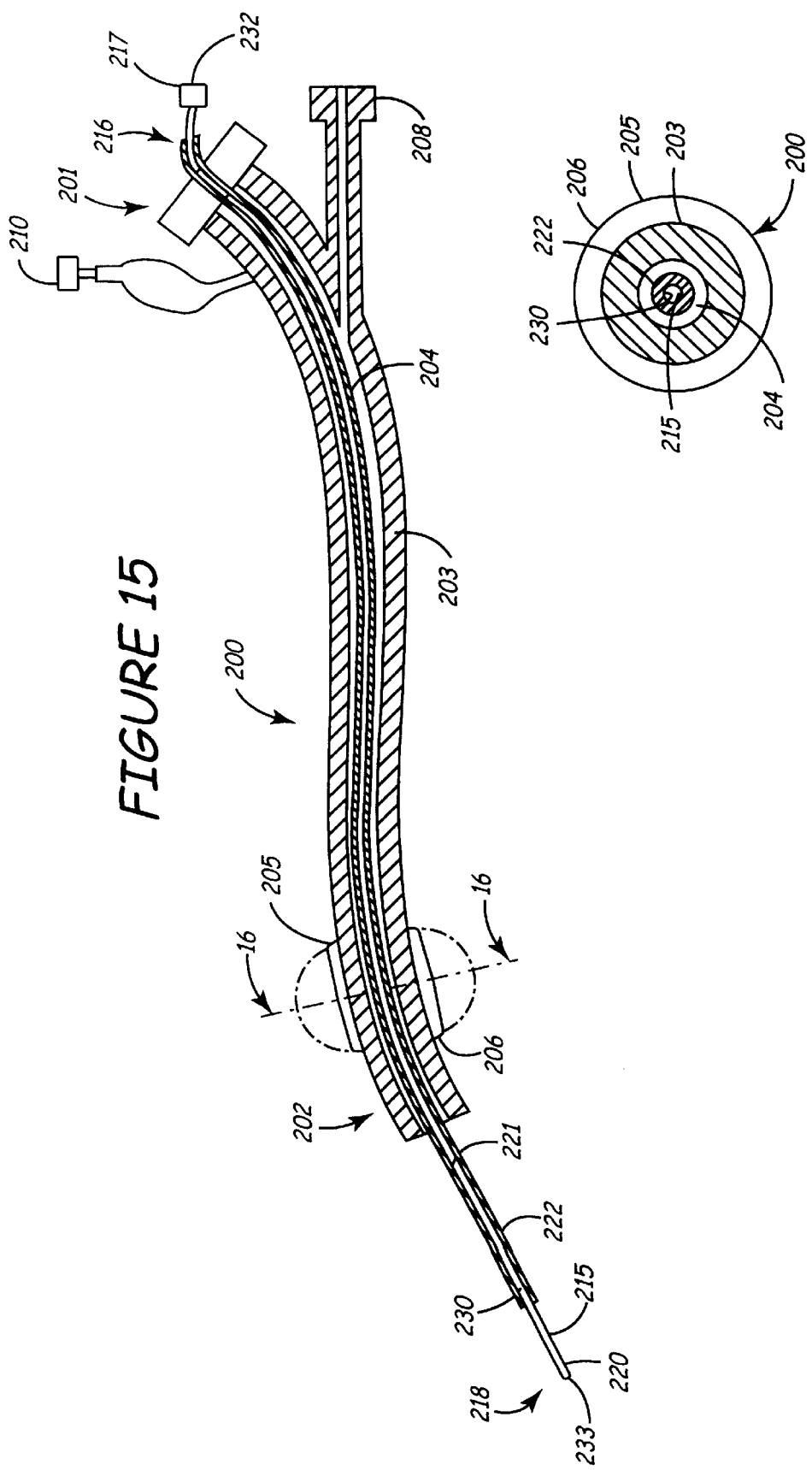

METHODS AND APPARATUS FOR TREATMENT OF PULMONARY CONDITIONS

CROSS-REFERENCE TO RELATED APPLICATIONS

This application is a continuation-in-part of U.S. Ser. No. 09/304,681, filed May 4, 1999, now U.S. Pat. No. 6,327,505, which claims priority to U.S. Provisional Application No. 60/084,580, filed on May 7, 1998, both applications being incorporated herein by reference.

FIELD OF THE INVENTION

The present invention relates generally to apparatuses and methods for treatment of physiological or pathological conditions through a body lumen. Specifically, the invention provides for treatment of pulmonary conditions through the lumen of a pulmonary airway by applying electrical energy, such as radio frequency (rf) energy, to a conductive fluid passed into the airway.

BACKGROUND OF THE INVENTION

Humans are beset with a variety of vascular and pulmonary conditions and abnormalities. Examples of some vascular abnormalities include arteriovenous malformations, arteriovenous fistulas, and aneurysms. Examples of pulmonary abnormalities or conditions include atelectasia, emphysema, pneumothorax, tumors, cysts, blebs and bullous diseases, etc.

Two very serious cerebral vascular ailments are arteriovenous malformations and aneurysms. Arterial-venous malformations, commonly referred to as AVMs, are a fibrous mass of intertwined, directly connected arterial and venous vessels. That is, the artery will branch into numerous smaller arterial vessels that in turn feed directly into the numerous veins. An AVM located in the brain therefore deprives certain areas of the brain of the blood needed for proper functioning. As the AVM steals blood from normal brain parenchyma, the theft of blood can create a variety of disease states or brain malfunctions, including but not limited to epilepsy and transient ischemic attacks. One of the considerable risks associated with AVM growth is that the AVM will burst, leading to intracerebral bleeding.

An aneurysm is an abnormal bulge in the wall of a blood vessel that develops as a result of a weakness in the vessel wall. Aneurysms can take two forms: sacular and fusiform wherein a portion of or the entire circumferential extent of the vessel wall is implicated, respectively. Aneurysms can rupture, leading to cerebral bleeding and can cause a patient to have a stroke or to die. An arteriovenous fistula is a direct fluid connection between an otherwise fluidically isolated artery and vein.

A number of techniques and procedures have been developed to deal with AVMs and aneurysms. Both have been treated through surgery. During a surgical procedure to treat an AVM, the skull is opened and the feeding arteries and outgoing veins are ligated. The AVM is then excised. This procedure will normally require some cutting and removal of brain tissue. In addition, there have been several minimally invasive procedures developed to treat these vascular ailments. For example, AVMs have been treated by inserting a catheter into a patient and guiding it to the location of the AVM. A glue is then released that forms a plug and blocks the artery feeding the AVM. The blood is diverted back into the normal blood flow path as a result.

Aneurysms have also been treated by various techniques. Surgical treatment of an aneurysm will typically involve exposing the aneurysm and then applying a clip to the neck of the aneurysm to close off the aneurysm from the vessel, thereby re-establishing normal circulating blood flow in the treated vessel. One minimally invasive procedure involves delivering a catheter to the point of the arterial or venous aneurysm and then releasing a coiled wire into the aneurysm itself. Once released, the wire uncoils to fill the aneurysm. Blood tends to clot around the coiled wire, thus sealing off the aneurysm. Another minimally invasive procedure, known as Hunterian ligation, involves placing a detachable balloon via a catheter at the location of the aneurysm, inflating the balloon, and then releasing it, thereby completely occluding the artery. Yet another minimally invasive procedure involves placing a detachable balloon inside the aneurysm itself, inflating it and detaching it.

While effective, the prior known techniques of treating vascular ailments, particularly cerebral vascular ailments, carries with them certain risks that are preferably avoided. For example, open cranial surgery carries with it risks of infection, hemorrhaging, anesthetic risks, organ function failure, stroke, paralysis and death. Minimally invasive procedures like treatment of AVMs with glue can be difficult because the blood flow through the AVM will inhibit the solidification of the glue at the proper location. In addition, the glue plug may loosen or dissolve over a time, leading to the reoccurrence of the AVM, that is, the recanalization or reopening of the previously occluded vessel. As for treating an aneurysm with a coiled wire, the wire is left in the brain in the midst of a forming clot. The clot or portions thereof can break away into the blood stream and can cause a stroke. In addition, the coiled wire has been known to spontaneously dislodge and migrate through the vascular system. Likewise, the use of a balloon to treat an aneurysm has its share of risks, among them premature balloon detachment, rupture after inflation and detachment, and migration. Migration can lead to an unexpected and undesired distal vessel occlusion, which can in turn lead to brain ischemia and ischemic stroke.

In summary, treatment of vascular abnormalities presently involves either surgical intervention or minimally invasive procedures that in some situations operate to occlude the vasculature (AVMs) and in others to occlude the abnormality itself (aneurysms). Both procedures offer the possibility of severe risks, however.

It has recently been proposed to use radio frequency electrical current for intraluminal procedures of blood vessels. U.S. Pat. No. 5,098,431 to Rydell is an example of such proposed use. Such proposals involve insertion of a current carrying guide wire into a lumen and then energizing the exposed electrode. As the temperature of the cells of the wall of the lumen increases, the cells begin to dry, leading to possible rupture of the cell walls. In this manner, the lumen could be severed. This use thus corresponds to electrocautery. The effects on the lumen with this procedure are difficult for the surgeon to control.

It is therefore desirable to have apparatuses and methods for treating body conditions including vascular, pulmonary, reproductive, etc. which are not subject to the foregoing disadvantages, which can be performed using minimally invasive surgical techniques, and which is safer than prior known techniques for treating such ailments.

SUMMARY OF THE INVENTION

Reduction, restriction, or occlusion of the various lumens being treated with electrical energy, such as radio frequency (rf) energy, coupled to the lumen walls with a conductive fluid, would reduce or eliminate some or all of the foregoing risk factors. According to the invention, a conductive fluid is introduced into a body lumen at a selected site for obtaining a desired effect on the lumen and/or surrounding tissues. An electrical current is then applied to the conductive fluid via an electrode electrically coupled to a current generator to create a virtual electrode. The virtual electrode carries the current to the walls of the vessel, pulmonary airway or other lumen wall. Typically, the greatest resistance or impedance to the flow of the current will be at the interface between the virtual electrode and the lumen wall, leading to initial heating at the site of the interface, that is, the walls.

As the resistance of the lumen walls leads to heating, the temperature of the walls begins to rise and the connective tissues found in the walls begin to depolymerize and shrink, causing the lumen to collapse inwardly in a radial direction and to shorten in a longitudinal direction. In this manner, a body lumen, or segment, or portion thereof, such as a blood vessel, fallopian tube or pulmonary airway (such as a bronchi or bronchiole), could be shrunk as desired to the point of being completely occluded. Depending on the power, frequency and duration of application of the current, tissues peripheral to the lumen can also be affected.

In one embodiment, an apparatus according to the present invention includes a catheter and a guide wire having, in one preferred embodiment, multiple segments of differing flexibility. The guide wire includes a conductive core having proximal and distal ends thereof. A first segment of the guide wire located at the most distal end thereof is exposed for the passage of radio frequency electrical current therefrom, thereby providing an electrode. An insulative material preferably formed of biocompatible polymers encases the guide wire from substantially the proximal end thereof to the first segment. In one preferred embodiment, the distal end of the insulative material includes varying thicknesses thereof to provide a varying flexibility to the distal end of the guide wire. For example, a guide wire in accord with the present invention may include a first insulated segment that has an insulative coating having a first radius and a second insulated segment located proximally of the first insulated segment that has a second radius that is greater than the first. Other segments having additional varying thicknesses may be included. Disposed within the insulating layer and extending substantially the entire length of the guide wire is at least one lumen for providing a conductive or electrolytic fluid to the target treatment site to form the virtual electrode.

A catheter that may be used with the present invention may include one or more lumens disposed in the catheter wall thereof. Such lumens may be used, for example, to provide an angiographic solution, an angioscope, and suction to a reduction/occlusion site.

In a method in accord with the present invention, a flow path for providing an rf conductive solution to a target treatment site in a body lumen is introduced into the body lumen. A conductive solution is delivered and an electrode is introduced into the lumen at the target reduction/occlusion site either simultaneously or subsequent to the introduction of the flow path for the conductive fluid. Radio frequency current is applied to the target site by a conductive electrode that is electrically connected to an rf power source through the conductive fluid, causing the connective tissues, such as but not limited to collagen and smooth muscle cells, in the lumen walls to heat and contract. Application of the rf current can be discontinued when the lumen wall has contracted or been reduced to the desired extent, which will often be complete occlusion. Alternatively, the rf current can be applied after contraction of the lumen wall to effect tissues peripheral to the lumen wall. Typically, to provide a permanent occlusion of a lumen, such as when an AVM is treated, the method will include the step of withdrawing proximally the conductive electrode, which typically will be made of a metal or metal alloy, during the application of rf power, and thus the virtual electrode, thus collapsing the lumen not only radially but longitudinally along its extent. Normally, the infusion will continue throughout the entire period of time that rf power is being supplied to the treatment site and will be discontinued only after the rf power has been discontinued.

In an alternative embodiment, the invention provides for treatment of a pulmonary condition through a pulmonary airway, such as a pulmonary bronchi or bronchiole. According to this embodiment, a monopolar or bi-polar electrosurgical device can be passed into a pulmonary airway to treat a pulmonary condition. An electroconductive fluid can be passed into he airway before or after passage of the electrosurgical device and the fluid then energized by the electrosurgical device to effect the airway and/or surrounding tissues.

BRIEF DESCRIPTION OF THE DRAWINGS

FIG. 15 is a longitudinal cross-section view of one embodiment of an electrosurgical apparatus according to the invention particularly suited for treating pulmonary conditions;

FIG. 16 is a transverse cross-section taken at line 16—16 of FIG. 15;

DETAILED DESCRIPTION OF THE INVENTION

Throughout the specification, guidance may be provided through lists of examples. In each instance, the recited list serves only as a representative group. It is not meant, however, that the list is exclusive.

Figure 1:
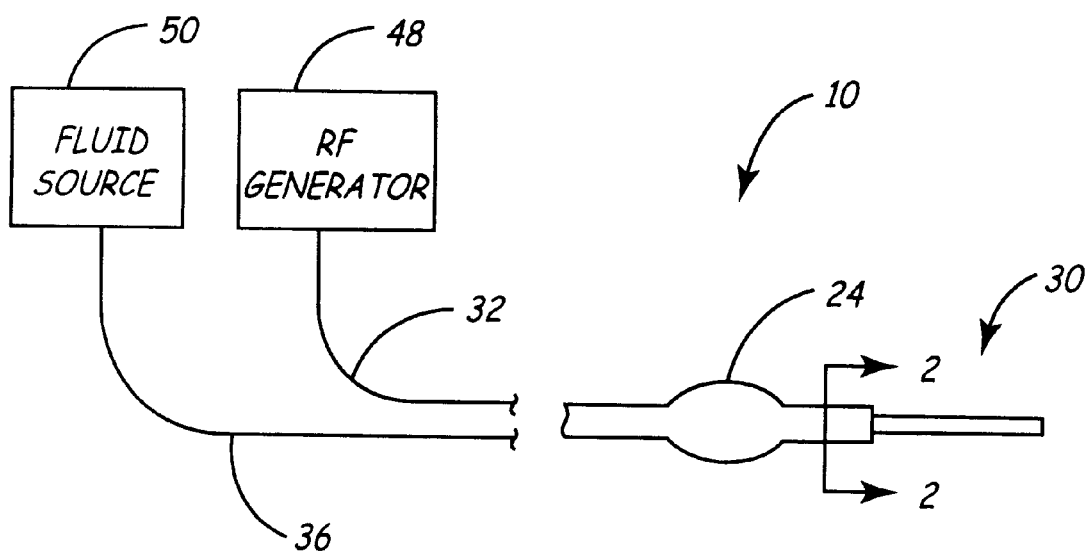
FIG. 1 is an illustration of an apparatus in accord with the present invention.
Figure 2:
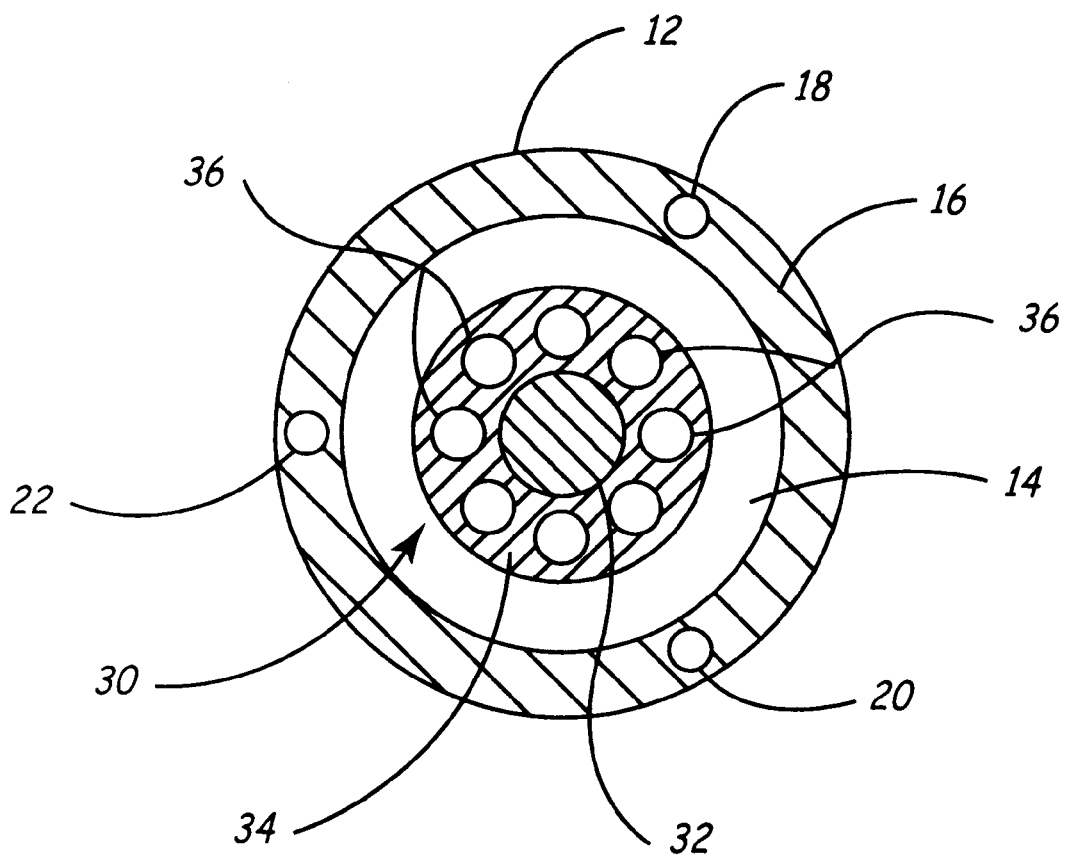
FIG. 2 is a cross-sectional view of the apparatus shown in FIG. 1 taken along viewing plane 2—2 thereof.

One embodiment of an apparatus 10 in accord with the present invention is illustrated in FIGS. 1–4. Apparatus 10 includes a catheter 12 including an interior lumen 14 disposed centrally therein. Typically, though not critical to the present invention, lumen 14 will be centrally disposed with respect to a circular cross section of catheter 12. Catheter 12 preferably includes a wall 16 having a substantially annular cross sectional configuration. Wall 16 may include disposed therein and running substantially the length thereof at least one lumen useful for providing a variety of functions. Thus, as seen in FIG. 2, catheter 12 may include lumens 18, 20, and 22. Lumen 18 may be provided, for example, for providing a pathway for air or a liquid such as saline to inflate a balloon 24, which is useful for temporarily locating catheter 12 within a vessel as known in the art and for inhibiting or stopping the passage of fluid within a body lumen in which the apparatus 10 is disposed. Lumen 20 may be provided to provide a suction or vacuum source for the removal of fluid as desired by the physician, as known in the art. Finally, lumen 22 may be provided for use by an angioscope, again as known in the art.

Disposed within catheter 12 is a guide wire 30. It will be observed that guide wire 30 does not completely occlude catheter lumen 14, thus enabling the volume surrounding guide wire 30 to function, if desired, as an infusion/flush lumen for angiography. Guide wire 30 will be movable in a proximal—distal direction within catheter lumen 14.

Guide wire 30 preferably includes an electrically conductive wire 32 encased within a sheath 34 made of a nonconductive material. Sheath 34 will include therein at least one microlumen 36. Microlumen 36 may be used as an infusion lumen for the delivery of fluids, vacuum or suction, or other uses. In the present embodiment it is contemplated that microlumens 36 may be used to supply a conductive or electrolytic fluid to the target site within a body lumen, such as a vascular abnormality as previously described or a fallopian tube, bronchiole, or other targeted area.

Figure 3:
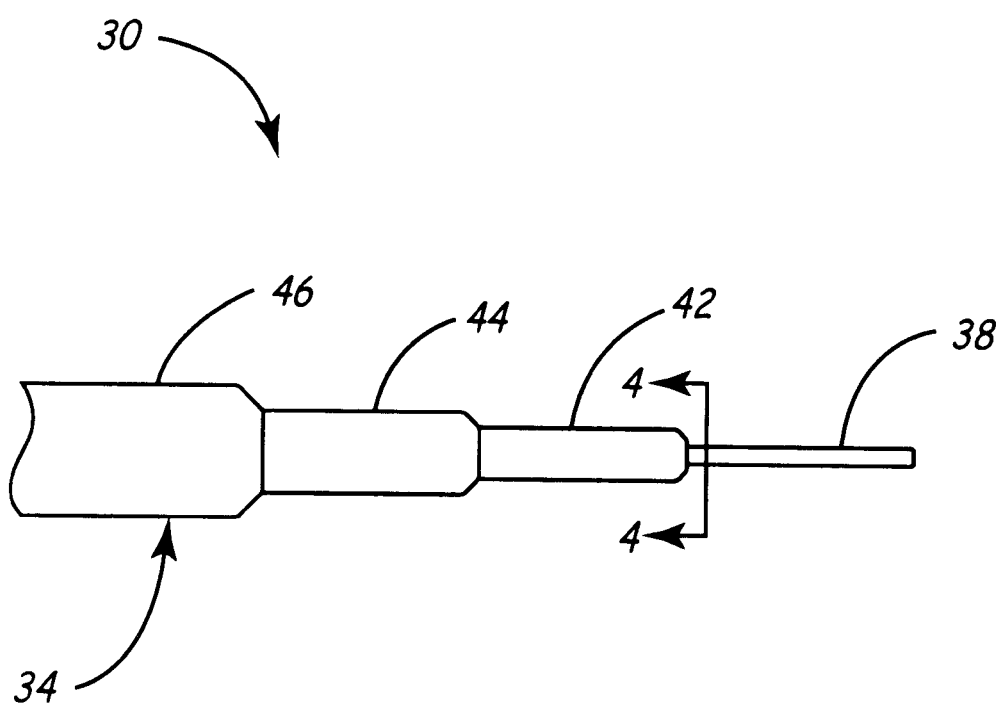
FIG. 3 is a view of the distal end of a guide wire for rf intraluminal reduction/occlusion in accord with the present invention.
Figure 4:
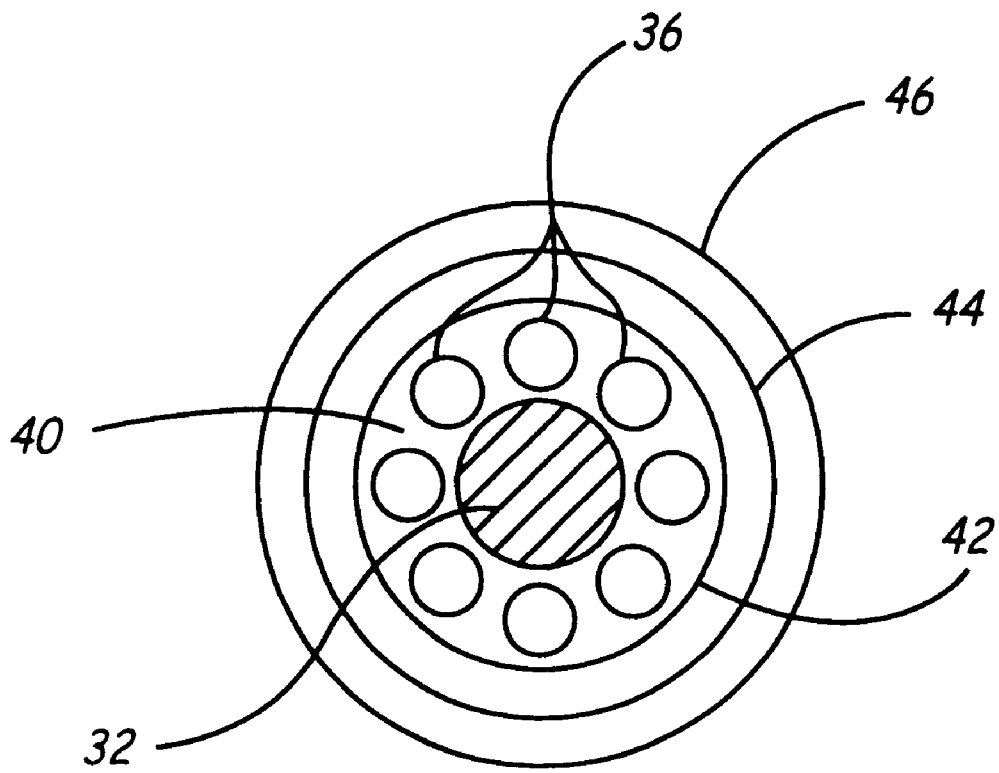
FIG. 4 is a cross sectional view of the guide wire of FIG. 3 taken along viewing plane 4—4 thereof.

Referring now to FIGS. 3 and 4, it will be observed that the distal end of the guide wire 30 includes an exposed wire or metal electrode 38. Electrode 38 may be formed of a solid wire, a wire mesh or braided material, or a coiled wire having either a circular or rectangular cross section, such as shown in FIGS. 12–15. Exposed wire electrode 38 extends from a distal end face 40 of sheath 34. Face 40 may be substantially flat but preferably will thicken in the proximal direction to provide a more gentle approach of the guide wire 30 to the vessel in which it is used.

It will be observed that sheath 34 thickens in radius as it extends from the face 40 to the proximal end of the catheter 34. As shown in FIGS. 3 and 4, sheath 34 has three distinct thickness segments, 42, 44, and 46. The varying thicknesses of sheath 34 provide varying degrees of flexibility or suppleness to the distal end of guide wire 30. This flexibility facilitates movement of guide wire 30 into position in the various body lumens, which in the case of the vasculature can include varied complex and sharp curves. Preferably, guide wire 30 will have at least two differing thicknesses to provide at least three different degrees of flexibility or suppleness.

Referring now to FIG. 1 again, it will be observed that guide wire 30 is electrically connected to a radio frequency current generator 48 and that microlumens 36 are fluidically connected to a conductive fluid source 50. Generator 48 and source 50 may be included within a single operating unit controlled by a microprocessor or computer in accord with the present invention.

It will be understood that the dimensions of apparatus 10 will vary with the intended use thereof. For example, treatment of small cerebral vessels will require a device appropriately sized. Where apparatus 10 is to be used in body lumens larger than a cerebral vessel, such as a fallopian tube, the dimensions will naturally be larger.

Figure 5:
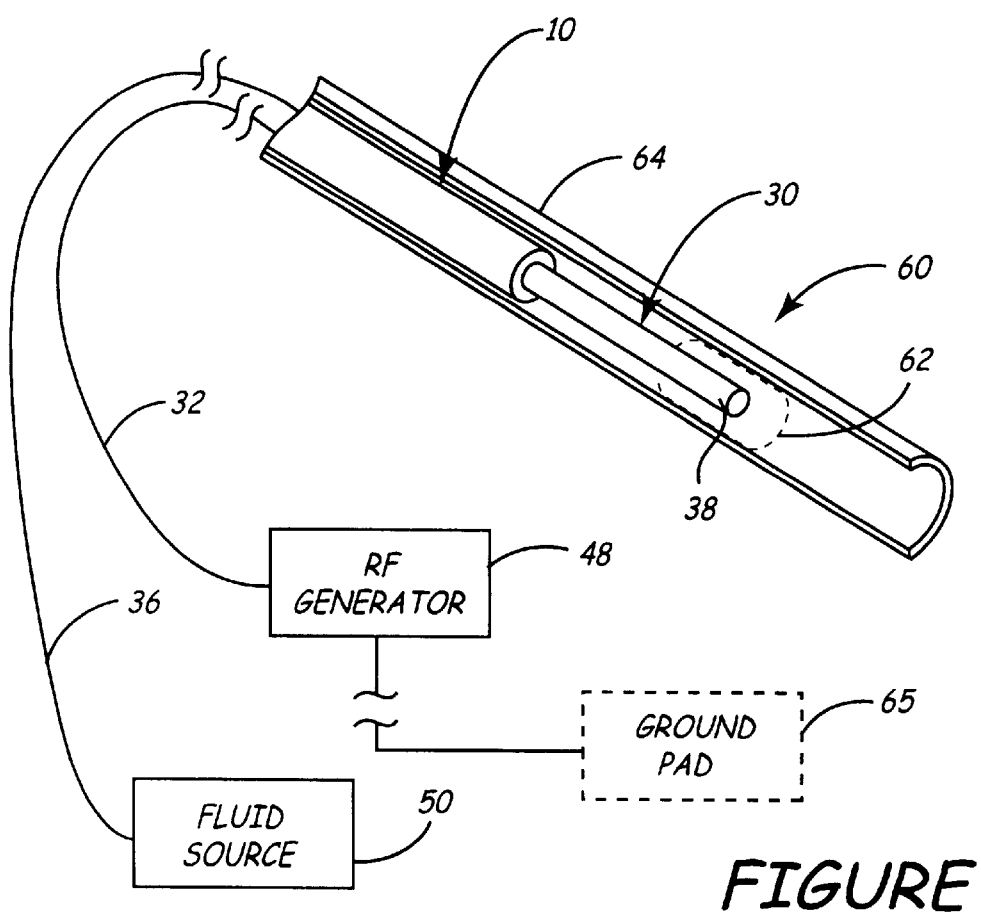
FIGS. 5–7 illustrate a method of occluding a lumen in accord with the present invention.
Figure 6:
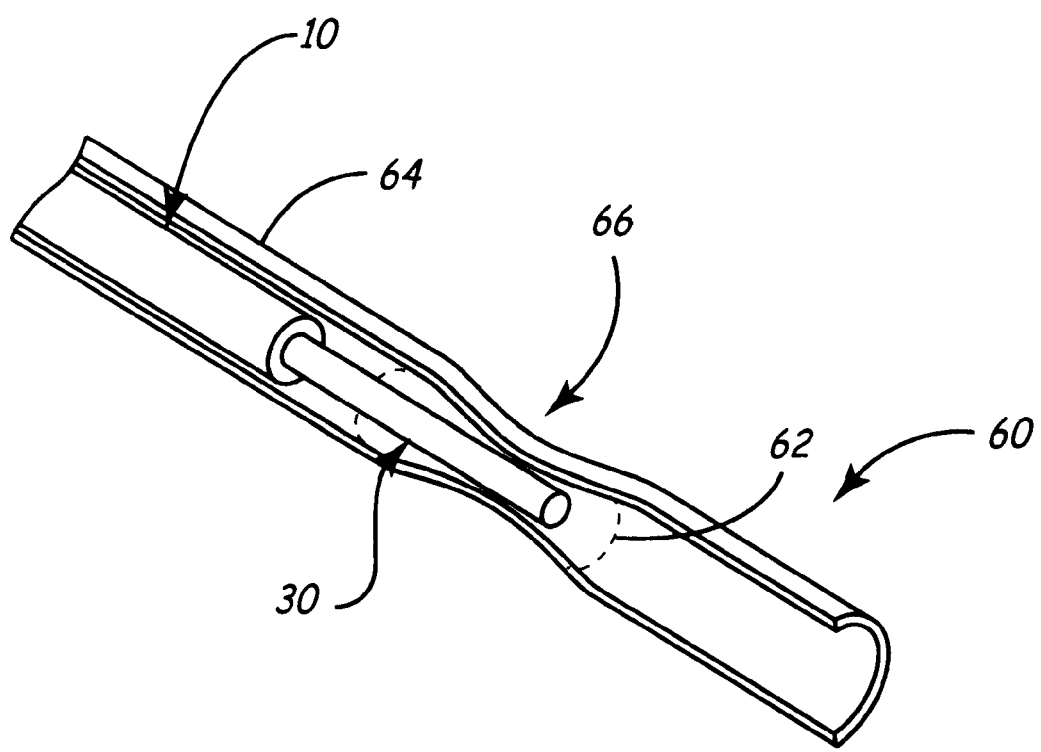
Figure 7:
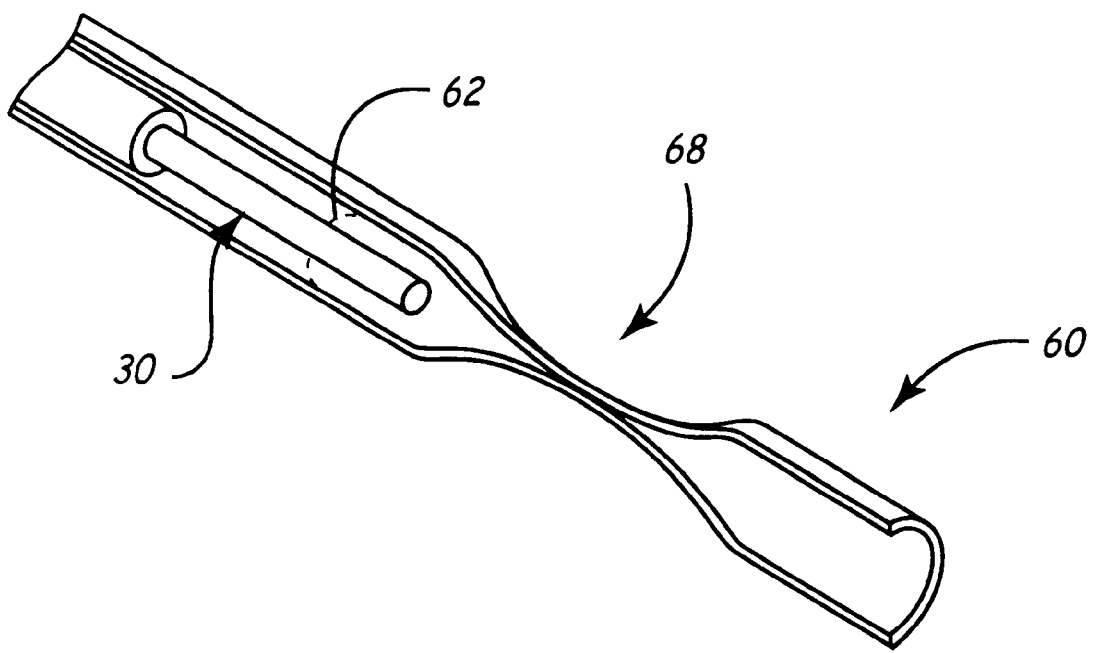

A method of treating a lumen in accord with the present invention is explained relative to FIGS. 5–7. In FIG. 5, apparatus 10 is shown in place within a body lumen 60 whose occlusion is desired. Located distally of the distal end (or electrode) 38 of the guide wire 30 may be an AVM if the lumen 60 is a cerebral vessel for example. Or lumen 60 may be a fallopian tube whose occlusion is desired for, for example, sterilization. As is known in minimally invasive procedures, typically apparatus 10 will be introduced to lumen 60 from a distant body location. For example, for certain cerebral vascular procedures, catheter 12 will be introduced into the femoral artery and moved to the proper location in the brain through navigation in the arterial system. As indicated by the dashed lines at 62, a conductive fluid (e.g., isotonic saline, hypertonic saline, Ringer's solution, etc.) by way of example only, will be provided to the lumen 60 by apparatus 10 from fluid source 50. An rf current will then be provided to conductive fluid 62, which will resultingly act as a virtual electrode to couple energy to a wall 64 of the lumen 60. It will be understood that where a monopolar electrode is being used, a ground pad 65 (shown only in phantom and only in FIG. 5 for ease of illustration) may be placed adjacent to the patient's body (not shown) to provide a return current flow path for the rf current from the electrode 38 to the rf current source 48. The present invention could also be used with a bi-polar electrode. As the wall 64 heats due to the inherent resistance thereof to the passage of the rf current, the connective tissues in the cells of the lumen wall 64 will begin to shrink, causing the lumen 60 to collapse or shrink radially inwardly in the area represented at 66, in FIG. 6. In addition, there will be a shrinkage of the lumen wall 64 in a longitudinal direction for the same reasons as given for the radial collapse.

Referring to FIG. 7, it will be observed that to avoid collapsing of the lumen 60 onto the guide wire 30, that guide wire 30 may be withdrawn slowly in the proximal direction. Should lumen 60 collapse onto guide wire 30, then it will be occluded only as long as the guide wire 30 remains in place. The subsequent withdrawal of the guide wire 30 will, in many instances, itself reopen or cause the reopening of the lumen 60. In addition, in many if not most applications of the present invention, it will be desired to collapse lumen 60 for a predetermined extent to reduce or eliminate the chance that lumen 60 will reopen. In such a circumstance, by slowly withdrawing guide wire 30 while continuing to provide conductive fluid within lumen 60 and rf current thereto, lumen 60 can be collapsed for an arbitrary distance at the discretion of the surgeon.

It will be observed that lumen 60 has shrunk or collapsed radially to such an extent that lumen 60 has been completely occluded in the area represented at 68. If lumen 60 were a cerebral artery feeding an AVM for example, then this procedure would result in the permanent closing of the feeding artery and allow the blood that had previously fed the AVM to be diverted to other, healthy brain tissue including that previously being starved of blood by the AVM. If lumen 60 were a fallopian tube, then the fallopian tube would have collapsed during the procedure, resulting in the sterilization of the woman undergoing the procedure.

It will be understood that conductive or electrolytic fluid will be delivered substantially continuously during the time that the rf current is being applied to the virtual electrode 62.

Figure 8:
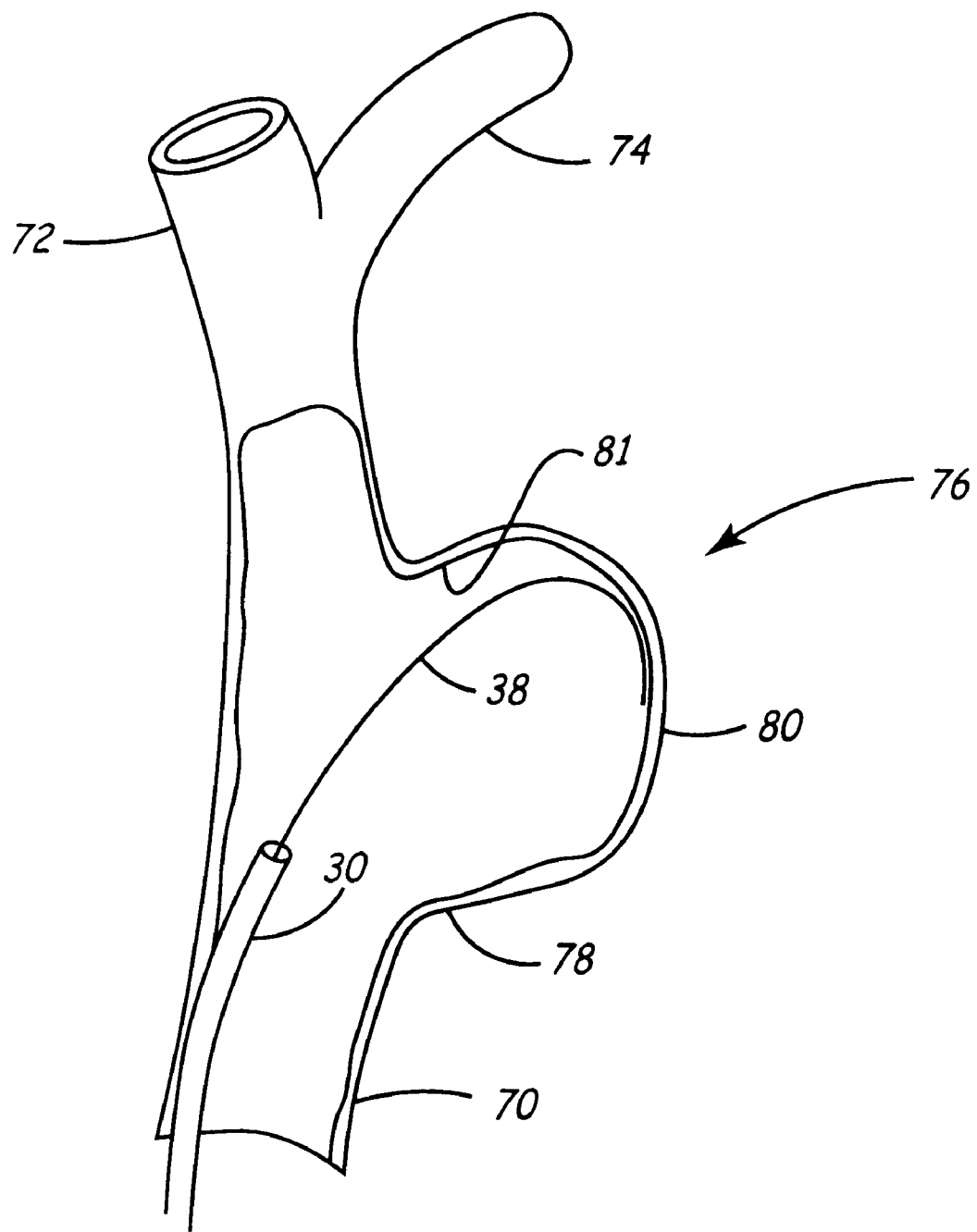
FIGS. 8–9 illustrate a method of treating a sacular aneurysm in accord with the present invention.
Figure 9:
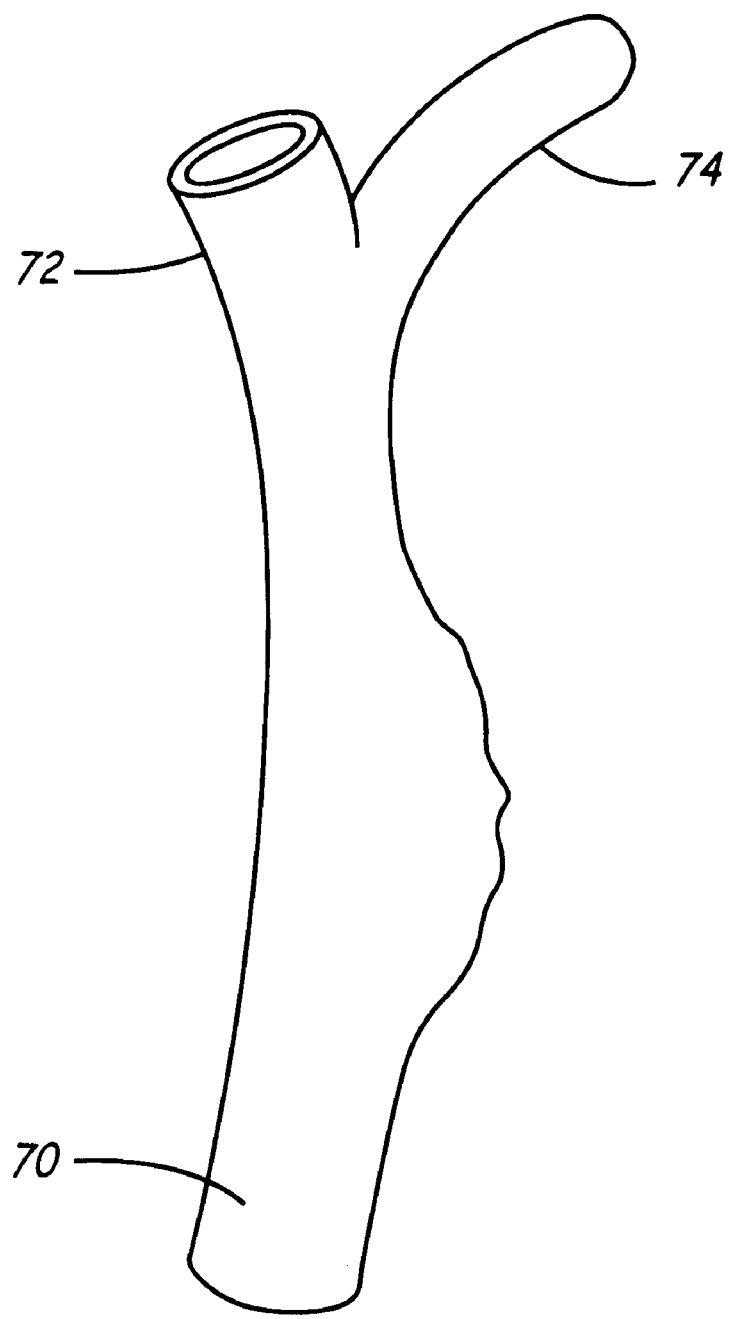

Turning to FIGS. 8–9, the use of the present invention to treat a sacular aneurysm will be explained. Thus, in the FIGS. it will be observed that a vessel 70 branches into smaller vessels 72 and 74. A sacular aneurysm 76 is shown located just prior to the branching of vessel 70 into vessels 72 and 74. Sacular aneurysm 76 has a neck 78 and an aneurysm wall 80.

In a method of treatment in accord with the present invention, a catheter 12 (not shown) will be inserted into the vascular system remotely from the aneurysm location, such as the femoral artery. Catheter 12 will be maneuvered close to the aneurysm location and then guide wire 30 will be extended therefrom. Electrode 38 is guided or steered into sacular aneurysm 76 through the neck 78. As electrode 38 enters the aneurysm 76 it will encounter an inner surface 81 of the aneurysm wall 80. Due to the flexibility of the electrode 38, electrode 38 will tend to curve backwards upon itself along inner vessel wall 81 as seen in the FIGs. Once it has been determined that electrode 38 is disposed closely adjacent to or is lying against aneurysm inner surface 81, the infusion of conductive fluid will begin to wash out the blood within aneurysm 76. After a predetermined infusion period, rf current will be supplied to electrode 38 in the manner hereinbefore previously described. The physiological effects on the wall 80 will be as previously described, with the heat engendering a shrinkage of the connective tissues in the cells forming aneurysm wall 80 of aneurysm 76. This shrinkage will cause the aneurysm 76 to shrink or collapse inwardly toward vessel 70, returning vessel 70 to a normal or more normal state, re-establishing normal blood flow within vessel 70, and reducing or eliminating the likelihood of rupture of aneurysm 76.

Figure 10:
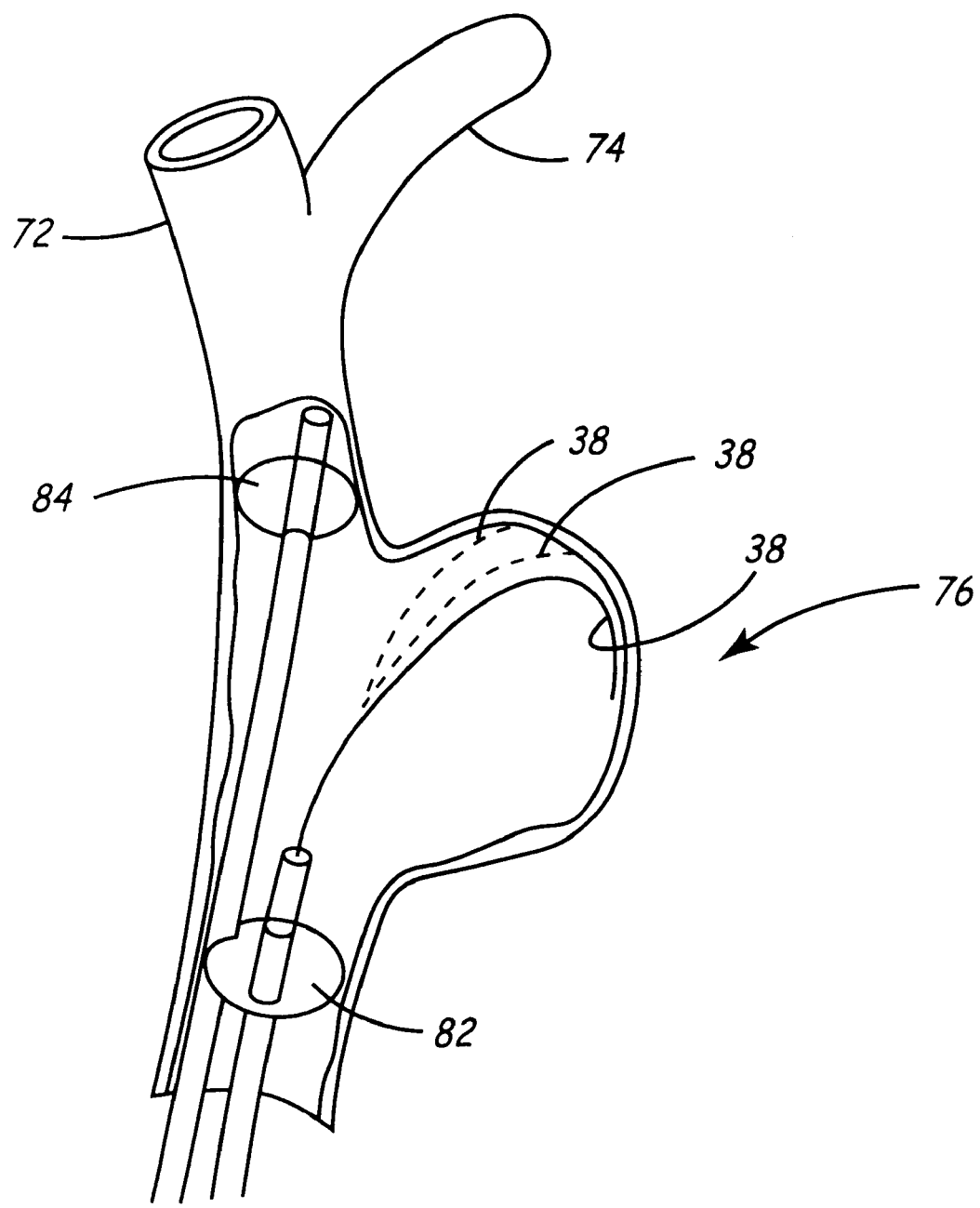
FIG. 10 illustrates treatment of an aneurysm according to the present invention using a dual balloon catheter system.

Referring to FIG. 10, an alternative embodiment of the present invention is used to treat an aneurysm 76 with a dual balloon catheter system. In this method, a first balloon 82 is inflated proximally of the electrode 38 to halt blood flow into aneurysm 76. A wash, which could comprise the conductive fluid, will then be dispensed by the catheter (not shown) to wash the blood within vessel 70 away. A second balloon 84 will then be inflated distally of the electrode 38 and the conductive fluid will be dispensed to fill the vessel 70 between the balloons 82 and 84—including aneurysm 76—with conductive fluid. Electrode 38 can then be positioned, or it could be positioned prior to inflation of one or both balloons 82, 84 within aneurysm 76 as previously described. The rf power can then be initiated and aneurysm 76 shrunk as previously described. As shown in FIG. 10, electrode 38 may be maneuvered to various locations within aneurysm 76 to effectuate more complete shrinkage. After aneurysm 76 has been shrunk to the desired extent, balloons 82, 84 will be deflated and retracted along with guide wire 30.

Figure 11:
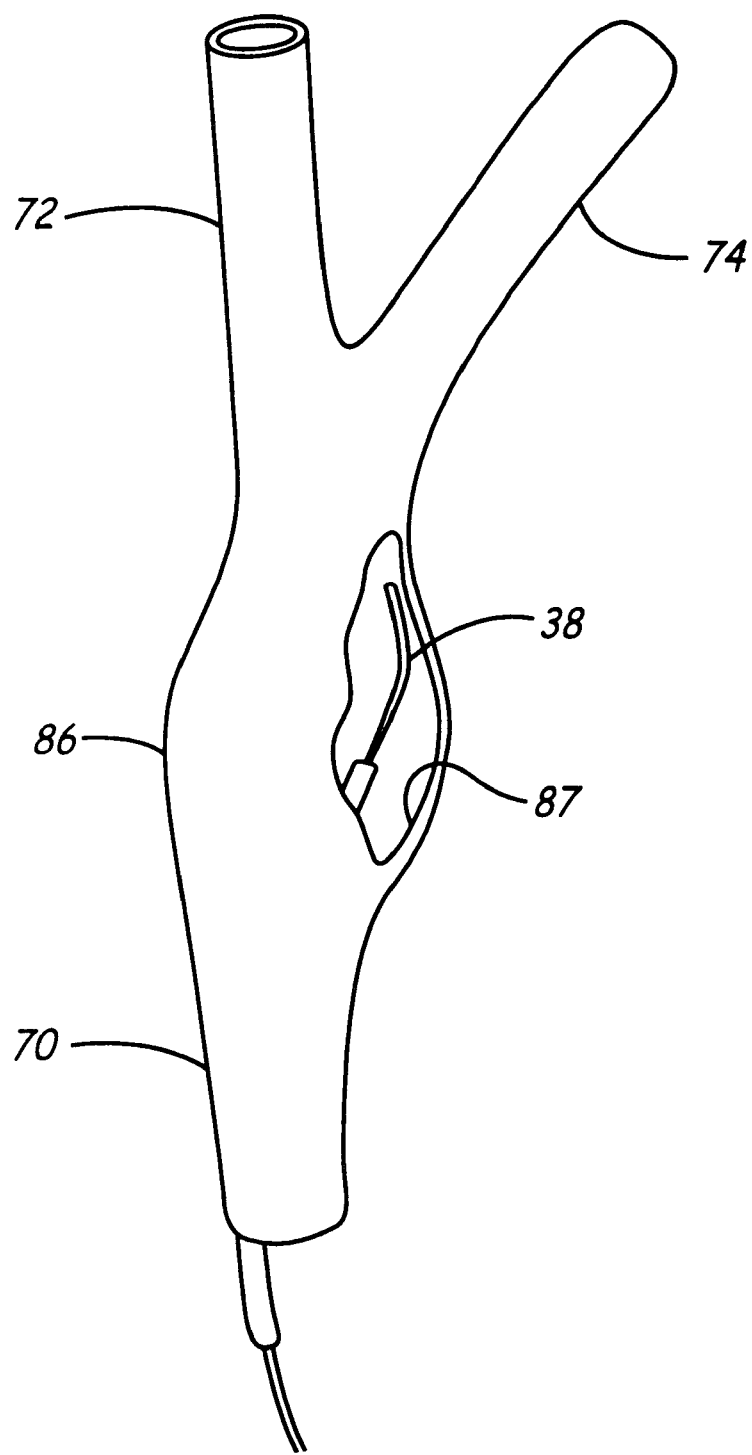
FIG. 11 illustrates treatment of a fusiform aneurysm according to the present invention.

Referring now to FIG. 11, a method of treating a fusiform aneurysm will be described. Thus, as shown in the FIGURE, vessel 70 includes a fusiform aneurysm 86. In this procedure, electrode 38 will be disposed against an inner wall 87 of aneurysm 86 and current will be applied to shrink the connective tissues in the area of power application. When a desired amount of shrinkage has occurred, electrode 38 will be repositioned and current will be reapplied. Electrode 38 will be moved around aneurysm 86 until the desired amount of shrinkage has occurred throughout the circumferential extent of aneurysm 86.

It will be understood that in treatment of AVMs, then, that the vessel is preferably completely occluded. The treatment of aneurysms, on the other hand, will normally not require complete occlusion of the lumen and may not in fact be desirable in many instances. Where the body lumen being treated is a fallopian tube, either a complete occlusion or a reduction in tube diameter sufficient to prevent passage of the egg would be sufficient. Where complete occlusion of the fallopian tube or other body lumen is not deemed desirable, then the dual balloon catheter method of treatment outlined relative to FIGS. 10 and 11 could be used.

In addition to the foregoing uses, the apparatus 10 could also be used to treat fistulas by reducing the size of the hole forming the fistula. Other intraluminal uses for the present invention include collapsing varicose veins and bronchioles.

Figure 12:
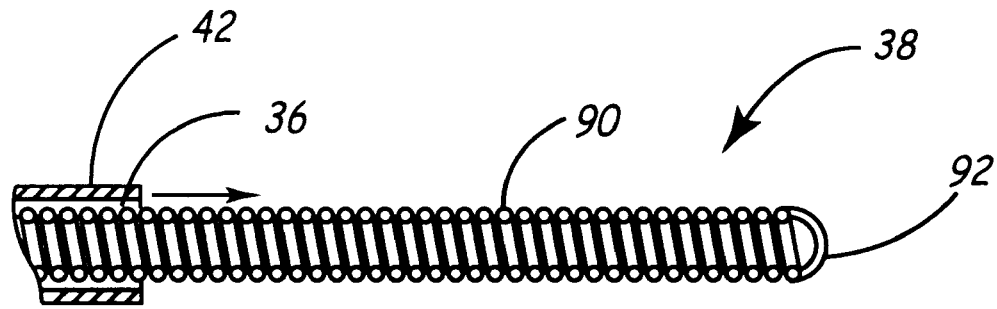
FIGS. 12–14 illustrate alternative embodiments of an active electrode for use in accord with the present invention.

Referring now to FIGS. 12–15, alternatives for electrode 38 will be described. FIG. 12 illustrates an electrode 38 formed from a wire coil 90 that is closed at a distal end 92 thereof by any known means. If desired, to manipulate the flexibility of coil 90 one or more adjacent coils could be attached to each other at selected positions along the exposed length thereof. In this one embodiment, microlumen 36 is adjacent wire coil 90, formed by sheath 34 (segment 42 of which is depicted in FIG. 12).

Figure 13:
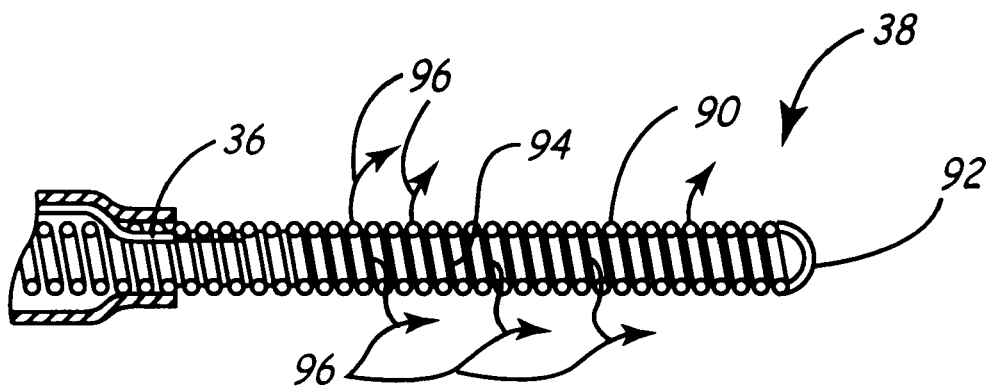

FIG. 13 shows another alternative embodiment of the distal end portion (or electrode) 38 of guide wire 30. In this embodiment at least one microlumen 36 is fed into an interior passage 94 of coil 90 by passing it between individual coils thereof. The conductive or electrolytic fluid would thus empty from a distal end of microlumen 36 into coil 90. The pressure head of the fluid would force the fluid between the individual coils as indicated by arrows 96 and out into the lumen of the vessel to be treated. As with the coil 90 shown in FIG. 12, if desired, to manipulate the flexibility of coil 90 of FIG. 13 and/or to control the distribution of the conductive fluid, one or more adjacent coils could be attached to each other at selected positions along the exposed length thereof.

While coil 90 has been shown as being formed of a wire having a circular cross section, it will be understood that a wire having a rectangular cross section could also be used in accord with the present invention to form the coil.

Figure 14:
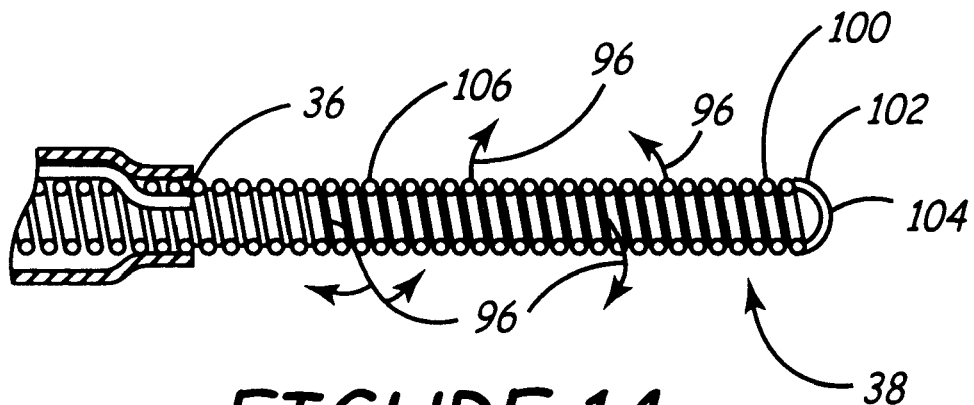

FIG. 14 illustrates yet another embodiment of the distal end of guide wire 30 wherein the electrode 38 is formed from a pair of concentrically engaged coils 100, 102, both of which are enclosed at the most distal end 104 as discussed relative to coil 90. As with the embodiment shown in FIG. 13, at least one microlumen 36 is fed into the interior passage 106 of the inner coil 102. The conductive fluid will empty from the microlumen 36 into the interior passage and under the influence of the pressure head provided by fluid source 50 (FIG. 5) will pass between the coils of coil 102 and coil 100 and into the lumen to be treated as indicated by arrows 96.

It will be understood that the wire coils 90, 100, and 112 may extend proximally to the appropriate electrical connection to rf generator 48 (FIG. 5), or they may be attached in any known way to any other electrical conduit with just the active, uninsulated portion being formed thereby. For example, each of the coils 90, 100, and 102 could be electrically connected to a solid wire extending proximally to the rf generator 48.

In another embodiment, the present invention can be advantageously used to treat a pulmonary condition through a pulmonary airway such as a pulmonary bronchi or bronchiole. Examples of conditions suitable for treatment according to the invention include: emphysema, pneumothorax, tumors, cysts, blebs, bullous diseases, etc.

According to this embodiment, in addition to collapsing the lumen of the airway, depending on the power, frequency and duration of the energy applied, pulmonary blood vessels, pulmonary alveoli and other pulmonary tissues peripheral to the airway lumen can also be affected. Thus, in some embodiments, the methods disclosed provide for lung volume reduction of a portion of the lung supplied by one or more pulmonary airways treated according to the invention.

In many embodiments, the invention can advantageously be performed through minimally invasive procedures including accessing the pulmonary airways via the trachea or through a minimally invasive thoracic incision. In some preferred embodiments, the invention can be performed through a bronchoscope passed into the lung via the trachea.

As a review of the air conducting system of the lung, after entering the nose and/or mouth, air moves through the pharynx and larynx into the trachea and through the bronchi and bronchioles until ultimately entering the alveoli where gas exchange between blood and the atmosphere occurs. In humans, the trachea bifurcates at the carina into a right main bronchus in the right lung and a left main bronchus in the left lung. Each main bronchi divides into secondary or lobar bronchi (two on the left, three on the right) which supply a lobe of the lung. Each lobar bronchus further divides into tertiary (segmental) bronchi which supply specific bronchopulmonary segments. Within each segment there is further branching of the bronchi into bronchioles (conducting, terminal and respiratory bronchioles) which lead to the alveolar ducts and sacs. Pulmonary blood vessels (i.e., pulmonary and bronchial arteries and veins) carry blood to and from the lungs and follow paths adjacent the pulmonary airways. Generally, the trachea and proximal bronchi comprise hyaline type cartilage which transitions into an elastic cartilage in the smaller airways and ultimately to smooth muscle closer to the alveoli. An elastic connective tissue frame work surrounding the airways and blood vessels enables the lungs to expand and contract during respiration.

In addition to the power, frequency and duration of the energy applied, the location of application of the energy, the number of airways to which treatment is applied and the surface area and location of the ground pad or return electrode can affect the amount of lung tissue treated according to the invention.

In some embodiments, the invention can be advantageously used to occlude airways and shrink portions of lung tissue which are poorly vascularized, poorly ventilated or do not permit effective oxygen exchange due to, for example, atelectasis (e.g., pneumothorax, bronchitis, pneumonia), emphysema, blebs, bullous disease, chronic obstructive pulmonary disease (COPD), etc. Accordingly, the invention can provide for the non-treated lung, diaphragm and chest cage to function more efficiently by improving airflow and allowing easier breathing.

In other embodiments, due to the proximity of the pulmonary blood vessels to the pulmonary airways, the methods disclosed can be used to occlude blood vessels which supply a portion of the lung, for example to starve a tumor infiltrating a segment of the lung supplied by the blood vessels.

One example of an apparatus particularly suited for this aspect of the invention is illustrated in FIGS. 15 and 16. FIG. 15 is a longitudinal cross-section view of electrosurgical device 200 and FIG. 16 is a transverse cross-section taken at line 16—16 of FIG. 15. Electrosurgical device 200 has a proximal end 201 and a distal end 202 and includes a catheter 203 having a lumen 204 extending from proximal end 201 to distal end 202. A lumen occluding mechanism 205 such as a balloon 206 is located at distal end 202. Balloon 206 can be selectively expanded or contracted by, for example, injecting a fluid (e.g., gas or liquid) through port 210 located near the proximal end 201 of catheter 203 using known arrangements for expanding and contracting balloons on catheters. Catheter 203 is preferably manufactured from a non-conductive material such as polyurethane, polyethylene terephthalate (PET), polytetra fluoroethylene (PTFE), etc. A fluid coupler 208 at the proximal end 201 of catheter 203 is in fluid communication with lumen 204 to permit injection or evacuation of fluids (gas or liquids), e.g., air, excess conductive fluid, into and/or out of the distal end 202 of catheter 203.

An electrode 215 is present and sized to pass within lumen 204 of catheter 203. The proximal end 216 of electrode 215 includes a power connector 217 for connecting electrode 215 to a power source, for example, an rf current generator (not shown). Electrode 215 includes a distal end 218 having a distal tip 220 configured to extend beyond the distal end 202 of catheter 203. Electrode 215 can be manufactured from any suitable conductive material, for example, stainless steel, carbon fibers, conductive polymers, platinum, tungsten, etc. In the illustrated embodiment, electrode 215 comprises a double wound helical coil 221 having an electrically insulated coating 222 extending substantially along the length of electrode 215 from the proximal end 216 to distal end 218. In this embodiment, insulated coating 222 does not extend to distal tip 220, thus leaving an exposed electrically conductive portion of electrode 215. For example, the distal tip 220 can comprise a non-insulated section at the distal end 218 of about 0.20 to 2.0 in length. Insulated coating materials suitable for insulating electrode 215 are known.

In the illustrated embodiment, electrode 215 can include a central lumen 230 extending from proximal end 216 to distal end 218. Lumen 230 provides for passage of a fluid from a fluid source (not shown) into fluid receptacle 232 at the proximal end 216 of electrode 215 through lumen 230 and out distal tip 220. In the illustrated embodiment, lumen 230 is sealed at the distal most aspect 233 of distal tip 220 using a suitable material such as epoxy, silicone, etc.

In the illustrated embodiment, spacing between coils of helical coil 221 permits release of the conductive fluid between coils at distal tip 220. In the proximal region, the insulated coating 222 of electrode 215 maintains a fluid within the lumen and the absence of the insulated coating 222 at the distal tip 220 permits release of the fluid from the lumen 230. Other arrangements for release of the fluid from the lumen can be used.

It will be appreciated that other electrosurgical devices can be used according to the method of the invention. For example, it is not necessary that the electrode be electrically conductive and deliver current to the fluid throughout the length of the lumen of the electrode. Rather, in one embodiment, the conducting fluid can be delivered to a distal end of a non-conductive catheter and an electrical current delivered to the fluid at the distal end of the catheter by a conductor as the fluid is exiting the catheter. In addition, while electrosurgical device 200 is illustrated as being monopolar (return electrode, being, for example, a ground pad), it will be appreciated that a bi-polar device could also be used.

In general the cross-sectional dimension of the distal end of an electrosurgical device according to this aspect of the invention is selected to permit passage of the distal tip into a selected location of a selected airway. Thus, for example, to starve a tumor or reduce a bronchopulmonary lung segment, a distal tip having a diameter of about 1 to 3 mm can be passed into a segmental bronchi having a lumen diameter of about 0.2 to 10 mm. In general, the airway diameters suitable for treatment according to the invention have a diameter range of about 1 to 15 mm. Typical distal tip diameters range from about 1 to 10 mm. The length of the electrosurgical device can vary, but is preferable of a length sufficient to access all regions of the lung.

In preferred embodiments, the electrical energy is provided by a radiofrequency (rf) electrical generator. The power of rf energy is provided at about 10 to 100 watts, typically about 50 watts at a frequency range of 0.30 to 3.0 MHz, typically about 0.5 MHz. The conductive fluid is delivered at about 0.5 to 5.0 cc/min, typically about 2.0 cc/mm The electrosurgical device can be passed into the patient's mouth or nose, through the pharynx, down the trachea and to the bifurcation of the trachea at the carina. At the carina, the operator can direct the device to the right or left lung and then proceed to advance into smaller pulmonary airways as determined necessary for a particular result or to treat a particular portion of the lung.

The device can be sized and configured to pass through a working channel of a bronchoscope to visually guide the device to a selected location through the bronchoscope. Alternatively, or in addition, the device can be guided to a selected location by tracking the device using known external visualization procedures including, for example, fluoroscopy, external ultrasound (e.g., two dimensional, real time, etc.), pulse-echo ultrasound scanning, etc. The electrosurgical device can also be positioned at a selected location within a pulmonary airway through an open chest procedure and palpation of the device as it is passed to a particular location either from the periphery of the lung through the thoracic opening or through the trachea distal to the periphery of the lung.

Once the distal tip is positioned within the lumen of a selected pulmonary airway, preferably, air is evacuated from the portion of lung to be treated. Air evacuation can be performed passively or actively. For example, "passive" evacuation of air can be performed on a patient being ventilated by removing the positive pressure airflow to the region of the lung to be treated. Lack of positive airflow will permit the region of lung not being ventilated to collapse. In general, "active" evacuation of air refers to aspirating or suctioning air from the region of the lung to be treated. Typically, the air is evacuated from the region of the lung distal to the selected site for treatment with the electrosurgical device.

Figure 17:
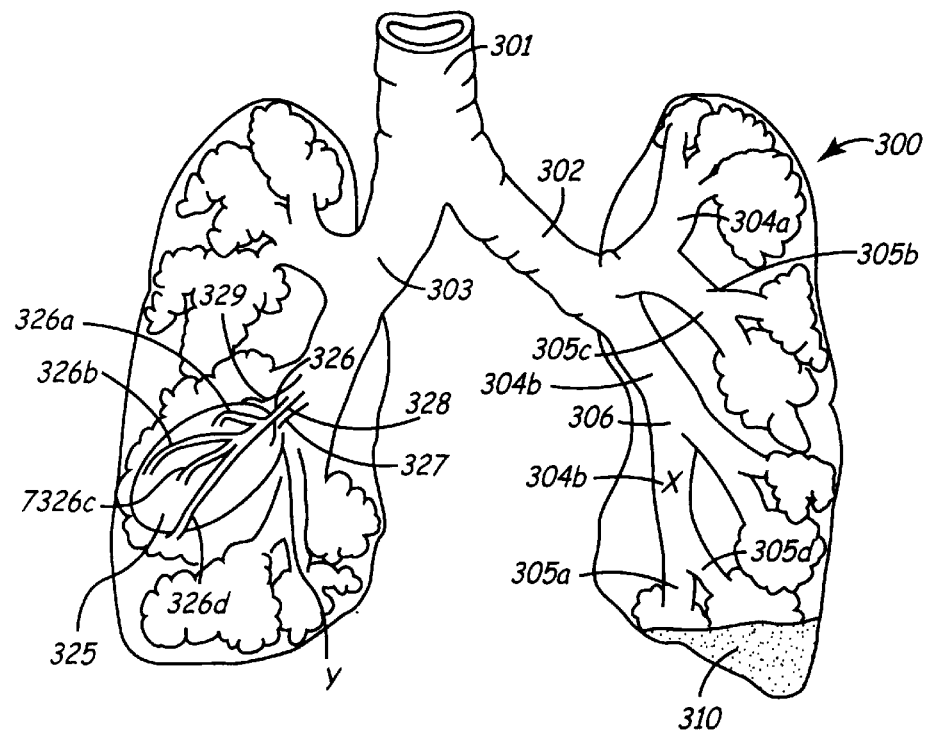
FIG. 17 is a diagrammatic representation of a lung.

The following discussion exemplifies methods of the invention using an electrosurgical device such as device 200 illustrated in FIGS. 15 and 16. Referring now to FIG. 17, there is illustrated a lung 300 including a trachea 301, left main bronchus 302 and right main bronchus 303. Left main bronchus 302 divides into lobar bronchi 304a and 304b which further divide into tertiary bronchi 305a–d. Stippled region 310 represents a portion of the lung to be treated according to the invention because it is non-functional due to, for example atelectasia, emphysema, blebs, bullous disease, COPD, etc. Such a portion of lung may be poorly perfused by blood or sufficiently perfused by blood but lack sufficient alveolar viability to permit oxygen transfer from the alveoli to the blood. Thus, in this situation, the method of the invention can be used to close off airways leading to non-viable alveoli and/or to close off blood vessels that perfuse non-viable alveoli.

Figure 18:
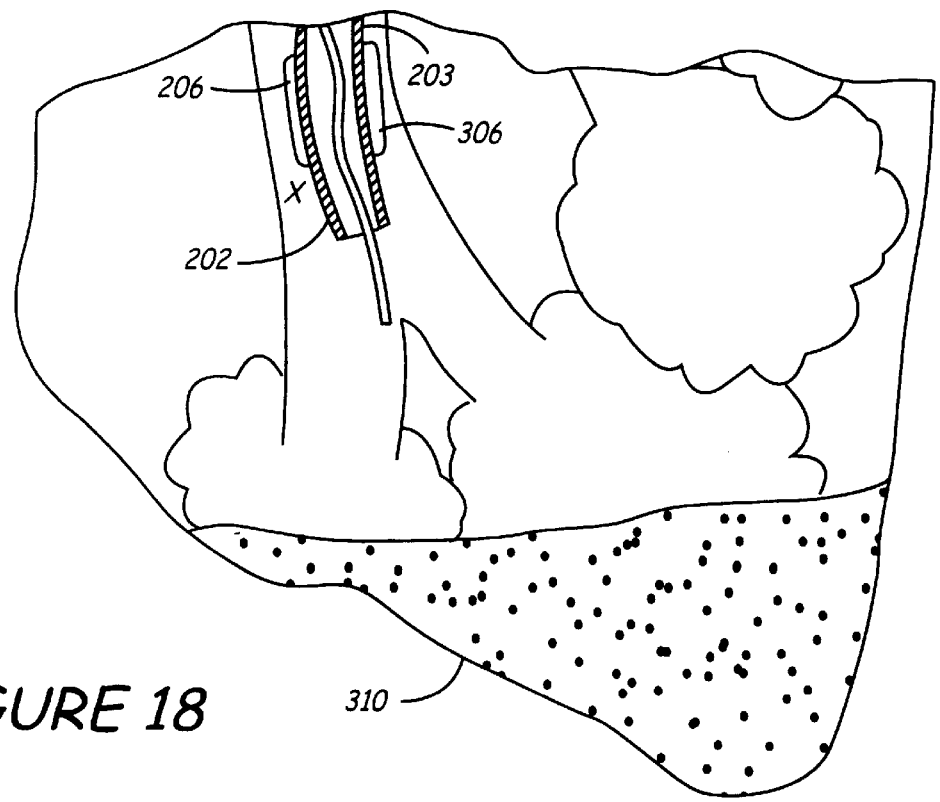
FIG. 18 is an enlarged view of a portion lung illustrated in FIG. 17 showing the positioning of an electrosurgical device in a pulmonary airway according to one embodiment of the invention.
Figure 19:
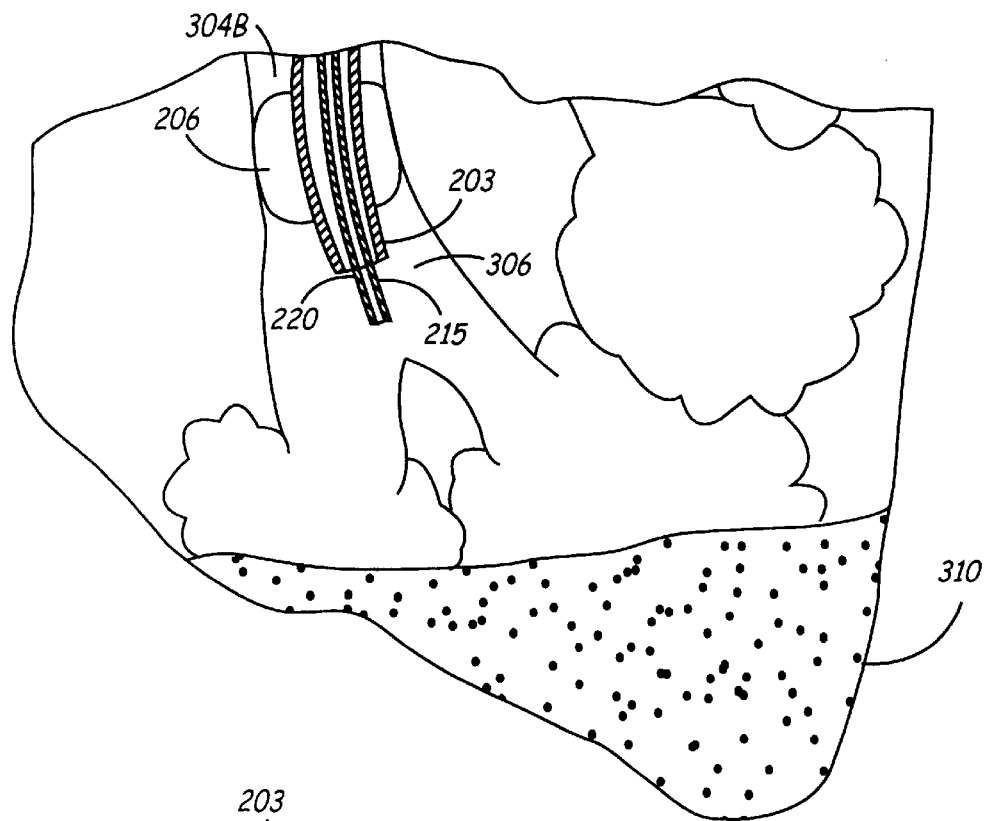
FIG. 19 is an illustration of the portion of lung and electrosurgical device illustrated in FIG. 18 showing an expanded balloon occluding the lumen of the pulmonary airway.
Figure 20:
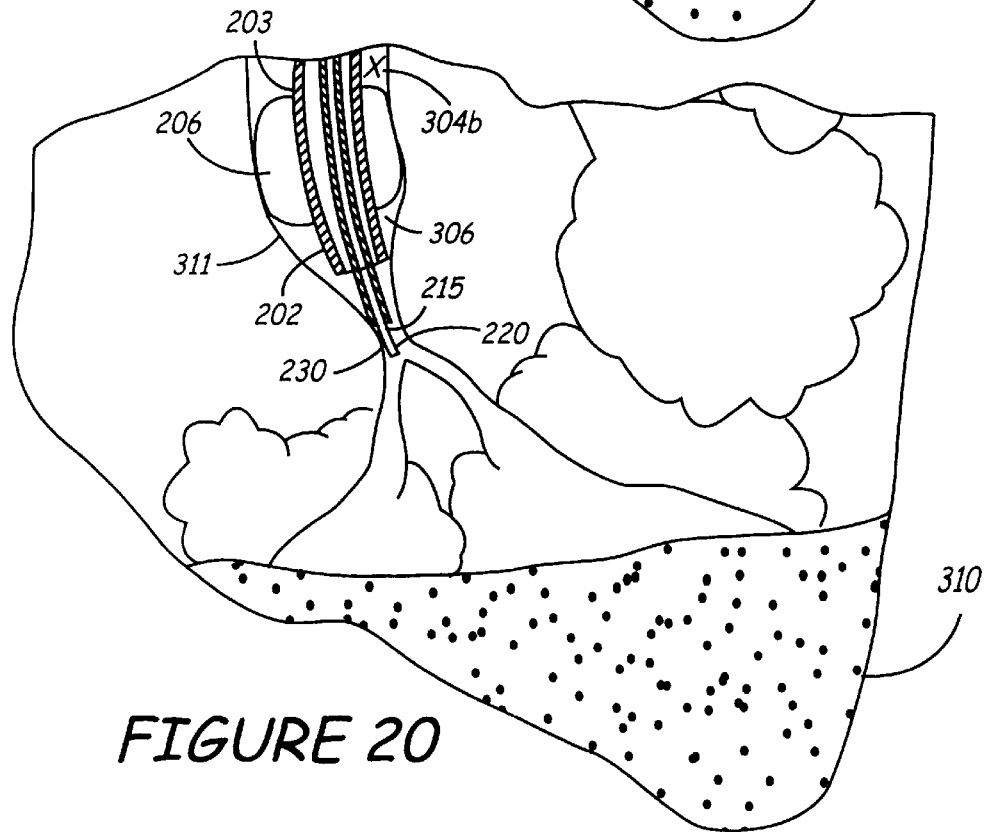
FIG. 20 is an illustration of the portion of lung of FIGS. 18 and 19 showing the pulmonary airway collapsed distal to the position of the electrosurgical device.

FIGS. 18–20 are enlarged views of region 310 of FIG. 17 and associated structures. To treat lung region 310, an electrosurgical device can be positioned at the region designated "X" of lumen 306 of lobar bronchi 304b. The distal end 202 of catheter 203 is positioned in lumen 306 such that balloon 206 is proximal to lung region 310. In this illustration, distal tip 220 of electrode 215 is shown extending distal to the distal end 202 of catheter 203. However, electrode 215 need not be in position until after collapse of the lumen as further described below.

Referring to FIG. 19, once catheter 203 is in position, balloon 206 can be inflated, using for example saline or air, to occlude lumen 306 of bronchi 304b. Air remaining in airways distal to the occluded lumen 306, can be removed passively or actively by aspiration of the air through fluid coupler 208 at the proximal end 201 of catheter 203 (FIG. 15). Also, it will be appreciated that the procedure can also be performed using a catheter that does not have a balloon. In such an embodiment, air in the lung distal to the distal end 202 of catheter 203 can be removed passively until lument 306 collapses.

As illustrated in FIG. 20, collapsed lumen 306 causes lumen walls 311 to be in close proximity to distal tip 220 of electrode 215. Fluid, preferably a conductive fluid, can then be passed through lumen 230 of electrode 215 and exit at distal tip 220 to provide fluid contact between electrode 215 and lumen wall 311. An electrical current (e.g., rf current) delivered to the distal tip 220 of electrode 215 will pass through the fluid to the lumen wall and cause shrinkage of the lumen wall around electrode 215. Delivering the current at a power of about 10 to 100 watts at a frequency of about 0.30 to 3.0 MHz for a period of about 5 to 50 seconds with a fluid flow rate of about 2 cc/min will cause occlusion of the lumen distal to the device. Continued delivery of fluid and current will cause tissues peripheral to the wall of the lumen 306 to shrink including pulmonary blood vessels. The amount of lung tissue reduced according to the invention can be visualized using non-invasive visualization methods (e.g., fluoroscopy, ultrasound), or alternatively, minimally invasive methods such as passing a thorascope into the thoracic cavity to visualize the lung as it is reduced.

Referring back to FIG. 17, in another embodiment, the method can be used to treat a pulmonary tumor. In this example, tumor 325 in the right lung is supplied by blood vessel 326 and vessel branches, 326a–326d. It will be appreciated that blood vessel 326 passes to tumor 325 in close proximity to bronchi 327. After passing the electrosurgical device into position Y of lumen 328 of bronchi 327, the airway distal to position Y can be passively or actively collapsed. A conductive fluid can then be passed between the electrode and lumen wall 329 and an rf current passed into the electrode. The rf current is carried by the conductive fluid to the wall 329 of lumen 328 to shrink lumen 328. After the lumen 328 has shrunk, continued application of rf current through the fluid will cause the energy to pass peripheral to lumen 328 and eventually occlude blood vessel 326. Once blood vessel 326 is occluded, flow to branches 326a–326d is stopped tumor 325 is "starved" due to a lack of blood supply.

In another embodiment, it will be appreciated that the methods of the invention can also be used to seal off all or a portion of lung which is non-functional due to a pneumothorax such as from a thoracic puncture, ruptured bulla, bleb, etc. By sealing off the non-functional lung, air and blood flow are delivered substantially towards portions of the lung where transfer of oxygen to the pulmonary capillaries can occur normally.

It will be appreciated that the foregoing discussion of the methods of the invention can be advantageously performed with a monopolar electrode. That is, the electrode 215 being an active electrode and a return electrode being positioned outside the patient's body such as known grounding pads. In addition, however, a bi-polar electrode can also be advantageously used. The bi-polar electrode can further provide control over the amount and uniformity of lung tissue treated. According to this embodiment, the active electrode can be passed into a pulmonary airway as previously described and a return electrode passed into the thoracic cavity on an exterior surface of the lung to be treated. Thus, the lung to be treated is bounded by the active electrode within the airway and the return electrode on the surface. This procedure also reduces the likelihood of inadvertent treatment of lung tissue proximate to the lung tissue to be treated but not intended for treatment. The return electrode can be passed through an open thoracotomy or through a minimally invasive incision, for example through a thorascopic channel. Providing access to the thorax also may advantageously provide for removal of treated lung.

The inventors also foresee that in some situations it may be advantageous to pass an active electrode into a first pulmonary airway and a return electrode into a second airway such that lung tissue between the electrodes can be treated according to the method of the invention solely through an intratracheal access rather than through thoracic opening.

From the foregoing detailed description and examples, it will be evident that modifications and variations can be made in the devices and methods of the invention without departing from the spirit or scope of the invention. Therefore, it is intended that all modifications and variations not departing from the spirit of the invention come within the scope of the claims and their equivalents.

What is claimed is:

1. A method for treating a pulmonary condition comprising:
   delivering a conductive fluid to a lumen of a pulmonary airway;
   applying electrical energy to the conductive fluid for an effective period of time to treat the pulmonary condition.
2. The method according to claim 1 wherein the electrical energy is radiofrequency (rf) energy.
3. The method according to claim 2 wherein the rf energy is applied by an electrosurgical device comprising:
   a catheter having a proximal end, a distal end and a lumen extending between the proximal and distal ends; and
   an electrode which can pass through the lumen for providing the rf energy to the conductive fluid.
4. The method according to claim 3 wherein the electrode has a proximal end which is attachable to an energy source and a distal tip for providing the rf energy to the conductive fluid.
5. The method according to claim 4 wherein the electrode includes a fluid passage for delivering the conductive fluid to the pulmonary airway.
6. The method according to claim 3 wherein the electrode is monopolar.
7. The method according to claim 2 wherein the pulmonary airway is a bronchiole.
8. The method according to claim 2 wherein the pulmonary airway is a bronchi.
9. The method according to claim 2 wherein the pulmonary condition is a pneumothorax.
10. The method according to claim 2 wherein the pulmonary condition is emphysema.
11. The method according to claim 1 wherein the electrical energy is applied for a period of time sufficient to occlude the pulmonary airway.
12. The method according to claim 1 wherein the electrical energy is applied for a period of time sufficient to shrink pulmonary tissue peripheral to the pulmonary airway.
13. The method according to claim 12 wherein the electrical energy is applied for a period of time and with power sufficient to occlude at least one pulmonary blood vessel peripheral to the pulmonary airway.
14. The method according to claim 12 wherein the pulmonary airway supplies blood to a pulmonary tumor.
15. The method according to claim 1 wherein the electrical energy is applied with a bi-polar electrosurgical device.
16. A method for treating a pulmonary condition, the method comprising the steps of:
   passing an electrosurgical device into a pulmonary airway supplying a portion of a lung;
   collapsing the portion of lung supplied by the airway;
   delivering a conductive fluid to the pulmonary airway;
   energizing the electrosurgical device to deliver electrical energy to the conductive fluid to treat the pulmonary condition.
17. The method according to claim 16 wherein the portion of lung is passively collapsed.
18. The method according to claim 16 wherein delivery of the electrical energy causes occlusion of blood vessels supplying blood to the portion of lung.
19. The method according to claim 18 wherein the portion of lung contains a tumor.
20. The method according to claim 16 wherein the device comprises:
   a catheter, the catheter having a proximal end, a distal end, a lumen passing from the proximal to distal end; and
   an electrode which passes through the lumen of the catheter.
21. The method according to claim 20 wherein the method is performed using a minimally invasive procedure.
22. The method according to claim 16 wherein the electrosurgical device is passed into the pulmonary airway to a position determined by using an external visualization system.

* * * * *